United States Patent [19]

Wilson

[11] 4,134,159

[45] Jan. 16, 1979

[54] TORQUE ABSORBER FOR ARTIFICIAL LIMBS

[76] Inventor: Michael T. Wilson, 1259 Monument Blvd., Concord, Calif. 94520

[21] Appl. No.: 805,059

[22] Filed: Jun. 9, 1977

[51] Int. Cl.² .............................................. A61F 1/08
[52] U.S. Cl. ................................................... 3/2; 3/18
[58] Field of Search .................. 3/2, 1.9, 1.912, 12, 3/17 R, 18, 26

[56] References Cited

U.S. PATENT DOCUMENTS

| 3,842,443 | 10/1974 | Weber | 3/2 |
| 3,947,897 | 4/1976 | Owens | 3/2 |
| 3,956,775 | 5/1976 | Moore | 3/2 |
| 4,038,705 | 8/1977 | Owens et al. | 3/2 |

OTHER PUBLICATIONS

"Ipos Hip Joint" brochure, Horace Dorrance Corp., P.O. Box 37, Campbell, Ca. 95008.

"Useful Rotation" brochure, Horace Dorrance Corp., P.O. Box 37, Campbell, Ca. 95008.
"U.S./Rancho Rotator", U.S. Mfg. Co., P.O. Box 110, 623 South Central Ave., Glendale, Ca. 91209, catalog p. 33B.

*Primary Examiner*—E. H. Eickholt
*Attorney, Agent, or Firm*—Phillips, Moore, Weissenberger, Lempio & Majestic

[57] ABSTRACT

A torque absorber for a lower limb prosthesis includes a retaining flange forming a portion of an assembly rotatably mounted in a hollow cylindrical member which may be adapted to receive a skeletal portion of a prosthesis. A resilient portion is bondingly formed about the hollow cylindrical member so that a plastomeric prosthetic socket or the like may be bondingly molded to the resilient portion and the retaining flange for cooperation therebetween to allow limited rotational motion of the prosthetic socket relative the hollow cylindrical member.

11 Claims, 6 Drawing Figures

U.S. Patent   Jan. 16, 1979   Sheet 1 of 2   4,134,159
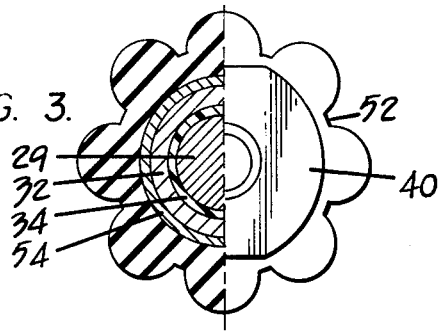
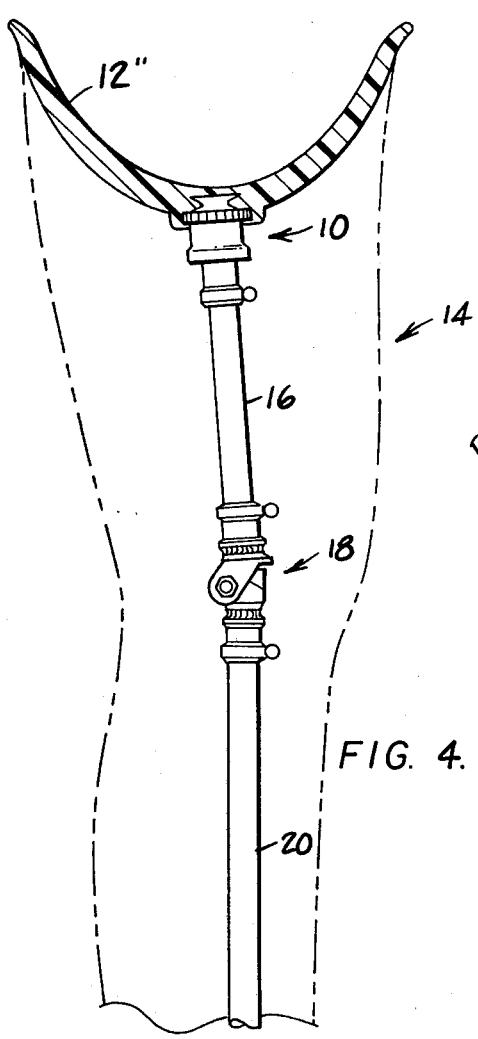
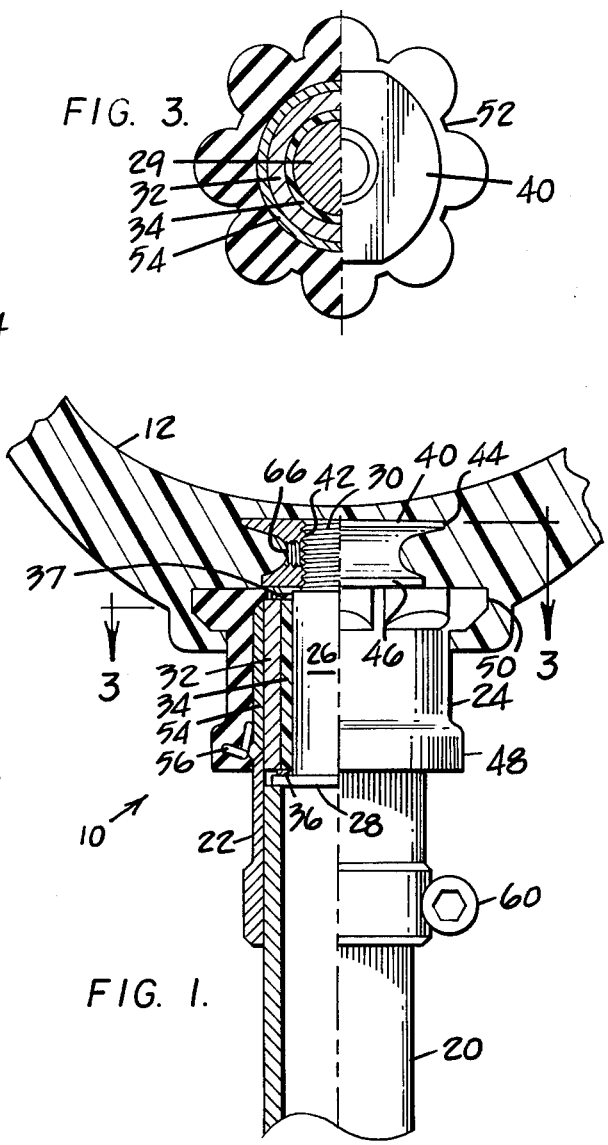
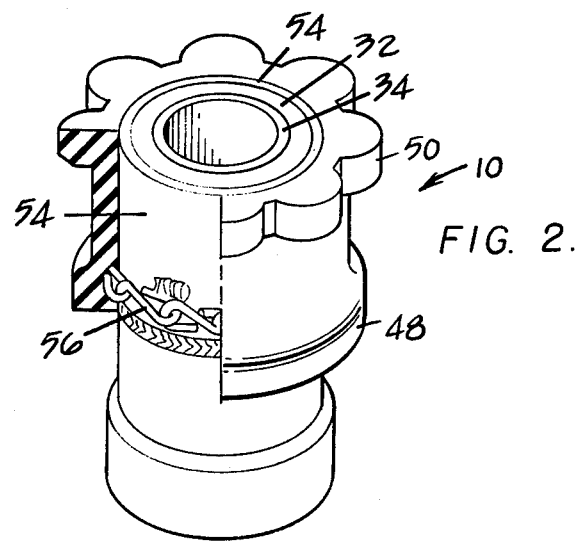

TORQUE ABSORBER FOR ARTIFICIAL LIMBS

BACKGROUND OF THE INVENTION

This invention relates to a device for interconnecting the socket of an artificial lower limb to the skeletal portion of the prosthesis. In particular, it relates to a torque absorbing device which permits limited rotational movement of the socket relative the skeletal portion.

Prosthetic lower limbs have progressed from rather crude exoskeletal devices to the present relatively sophisticated endoskeletal devices having a cosmetic outer surface closely approximating, at least visually, a normal human leg. In addition to the improvement of the structure of the prosthesis, development has progressed at the same pace in the necessary hardware to construct such an artificial prosthesis. The difficulties in the design and construction of such hardward are compounded in that the weight of the various elements must always be closely controlled while retaining the strength and the versatility of the various elements.

One unique problem encountered in a lower limb prosthesis is the rotational movement imparted to the prosthesis by the amputee swinging the stump with the subtending prosthesis in a para-saggital plane during walking. This rotational movement of the prosthesis is caused by the swinging of the hip of the amputee in order to walk. For example, as a leg is swung forward to take a step, the one hip swings forward relative the other hip. In view of the face that the entire pelvis is rotating about a vertical axis through the center of the hips and generally coincident with the line of intersection of the frontal plane and the saggital plane, a prosthesis subtending from a hip would also rotate about the same axis. When a prosthetic foot affixed to the prosthesis contacts the ground, the hip may be rotated 10-15° out of the frontal plane. As the amputee then lifts the other foot and swings the other leg forward, the other side of the hip will swing relatively forward, while the one side moves relatively backwardly. With no rotational capability of a prosthesis, the one prosthetic foot, which may have been placed on the ground in a relatively unnatural position, will remain in that unnatural position and may become more unnatural throughout the step with the other foot off the ground. If this were to be accepted, the stump of the amputee would rotate in the socket of the prosthesis. In addition to the awkwardness imparted to the walk, the forced rotation could prove to be discomforting to the amputee over an extended period of time.

Therefore, it has been found appropriate to include, at least in the endoskeletal type prosthesis, means to allow rotation of the prosthesis relative the socket. It is necessary, however, to install some sort of a resilient return means in such arrangements. In addition to the resiliency which must be imparted to the rotational device, means have to be provided in the device to permit mounting of the socket to the endoskeletal portion of the prosthesis. Commonly, this has been accomplished by a relatively large flat plate member made, in some cases, of wood to save weight. The flat plate member is then molded into the socket or screwed thereto by appropriate fastening means. In some cases the torque absorber or "rotator" as it is also called is positioned at the ankle thereby increasing the moment of the swinging leg to an almost unacceptable level.

It was with this problem in mind that the present invention was developed. Specifically, the problem of weight, compounded by the rather large plate member in the existing torque absorber joints which also may impart a high moment due to poor placement, and the resiliency requirement resulted in the present invention.

SUMMARY OF THE INVENTION

The present invention is for a prosthesis having a socket. It consists of a torque absorber comprising a first hollow cylindrical assembly for interconnection with the skeletal portion of a prosthesis, and a second assembly rotatably mounted in the first hollow cylindrical assembly. Bondingly associated about the first hollow cylindrical assembly is a resilient element. Such an assembly permits the prosthesis socket to be bondingly molded about the second assembly and the resilient element so that the second assembly and the resilient element cooperate to allow limited rotation of the socket relative the first hollow cylindrical assembly.

BRIEF DESCRIPTION OF THE DRAWINGS

FIG. 1 is an elevation view partly in section of the torque absorber which forms the basis for this invention.

FIG. 2 is a perspective view of a portion of the same torque absorber shown in FIG. 1 with a portion of the elastomeric member broken away.

FIG. 3 is a plan view of the torque absorber shown in FIG. 1 in relation to a portion of the complete prosthesis and mounted adjacent the socket.

FIG. 4 is an elevation view of the torque absorber shown in FIG. 1 adjacent a socket and also showing a pylon between the torque absorber and the knee.

DETAILED DESCRIPTION OF THE PREFERRED EMBODIMENT

Figure 6:
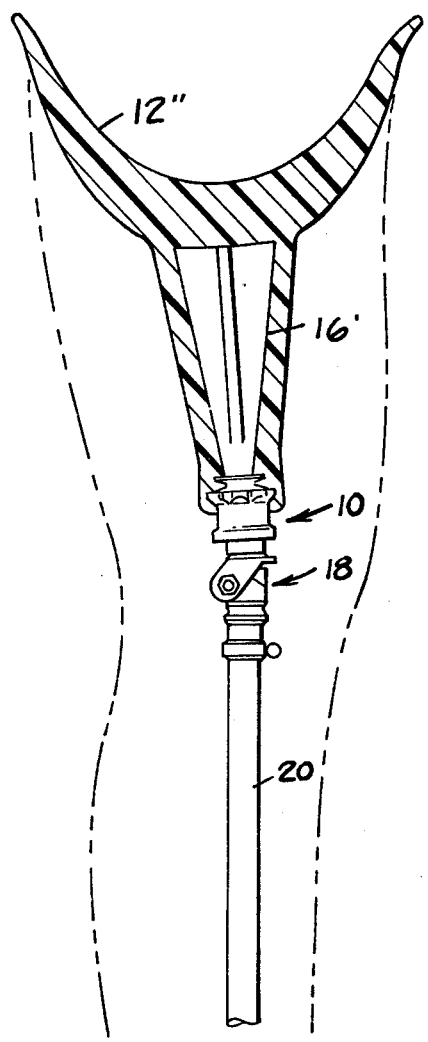
FIG. 6 is the embodiment shown in FIG. 5 with an interconnecting pylon between the knee and the socket.

Referring to FIG. 1, a torque absorber 10 in accord with the provisions of this invention is shown bondingly associated with the socket 12 of a prosthetic device 14. It can be seen from FIGS. 1, 4, 5 and 6 that prosthetic device 14 is comprised of endoskeletal elements which may include, for example, an upper pylon 16 or 16', a knee joint 18, and a lower pylon 20. In FIG. 1, the torque absorber 10 is shown associated with a pylon which may be pylon 16 but more probably is pylon 20 as denoted in FIG. 1 and applicable for a below-the-knee amputation.

Referring specifically to the structure in FIG. 1, it can be seen that torque absorber 10 is made up of means such as a hollow cylindrical member 22 for fixture to the skeletal portion of a prosthesis about which an elastomeric member 24 may be bondingly associated and to which a socket 12 may be bonded.

Interior of hollow cylindrical member 22 is an elongated cylindrical member 26 having a flanged end 28 and a threaded opposite end 30. Threaded opposite end 30 is of lesser diameter than the unthreaded mid-portion 29. Disposed between the elongated cylindrical member 26 and the hollow cylindrical member 22 is a press-fitted bushing 32 adjacent to the hollow cylindrical member 22 and a friction reducing plastomeric sleeve 34 between the elongated cylindrical member and the plastomeric sleeve. Such friction reducing material is well known in the art and will not further be described. Disposed between flanged end 28 and the press-fitted bushing 32 is a friction reducing plastomeric washer 36. Similarly, at the opposite end of the elongated cylindrical member 26 and proximate threaded end 30 is a second friction reducing plastomeric washer 37.

A retainer 40 having a threaded axial bore 42 is threadably positionable on threaded end 30. Retainer 40 has spatially separated flanges 44 and 46, the purpose of which will become apparent in the subsequent discussion.

Elastomeric member 24 is also formed with spatially separated flanges 48 and 50, with the flange 50 located at the end proximate retainer 40 and defining a plurality of grooves or serrations 52 circumferentially oriented about the elastomeric member.

It is desirable, although not necessary, that elastomeric member 24 extend above the end of press-fitted bushing 32. Furthermore, it is desirable, but not necessary, that the unthreaded mid-portion 29 of elongated cylindrical member 26 be sufficiently long to extend above the press-fitted bushing 32, but not to the height of the elastomeric member 24. Finally, the plastomeric washer 37 may be thinner than the stepped portion of elongated cylindrical member 26 formed by the unthreaded mid-portion 29 extending above the press-fitted bushing 32. The purpose of these dimensions is so that retainer 40 may be tightened on the threaded end 30 contacting first the elastomeric member 24 to seal the plastomeric washer 37 and press-fitted bushing 32 from plastomeric material utilized to construct socket 12. This will become more apparent in the discussion that follows.

In view of the turning moment which may be imposed upon elastomeric member 24, it is desirable to include a metallic gripping portion fixedly associated with the first cylindrical portions 54 of hollow cylindrical member 22. The metallic gripping portion 56 may be constructed of a plurality of flexible links in the form of a chain for bonding with first cylindrical portion by welding or the like.

The hollow cylindrical member 22 extends downwardly below the elastomeric member 24 and has formed at the lower end thereof clamping means 60 for fixture to pylon 20.

Figure 5:
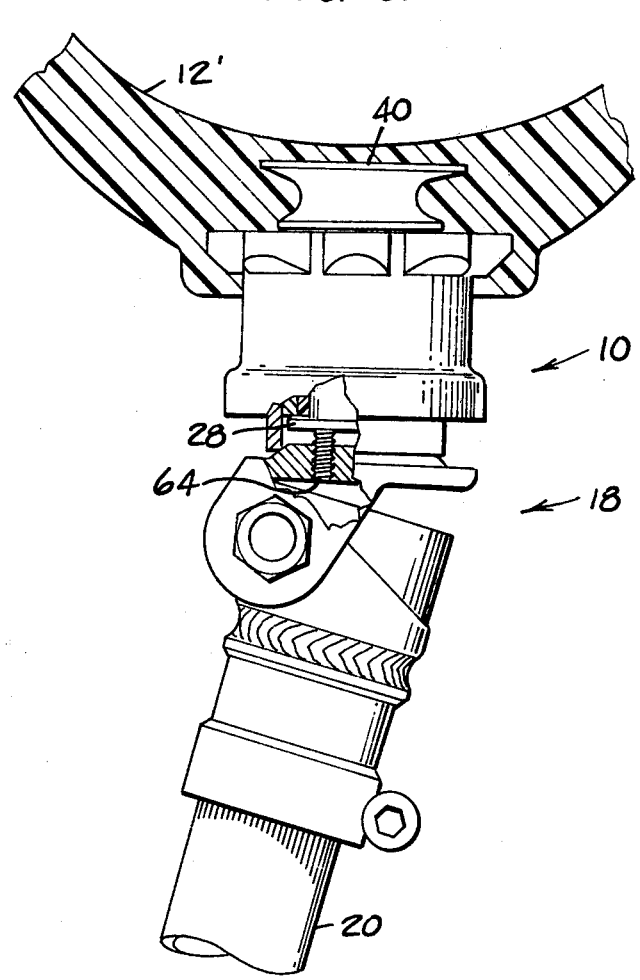
FIG. 5 is the same torque absorber shown in FIG. 1 mounted directly on a prosthetic knee joint.

Referring to FIG. 5, the same torque absorber 10 is shown relative an articulated knee joint 18. This structure is in the event of a long upper stump remaining on the amputee with only the loss of the knee joint and the lower limb and is preferable in any above-the-knee amputation when used in conjunction with the foamed plastic pylon 16' shown in FIG. 6. In this instance, the hollow cylindrical member 22 is affixed directly to the knee joint 18 by welding or the like. The method for affixing the knee joint to a lower pylon 20 is the subject of co-pending application Ser. No. 805,058. It will become apparent in the subsequent discussion that it is necessary to lock the retainer 40 relative the hollow cylindrical member during the molding process of a socket 12'. Consequently, when utilized in a knee joint application such as illustrated in FIG. 5, it is appropriate to provide a set screw 64 which may be tightened against flanged end 28.

Finally, it is appropriate to lock retainer 40 to threaded end 30 before molding socket 12. Accordingly, a set screw 66 has been found appropriate to accomplish this end. Set screw 66 is radially oriented between flange 44 and 46 and may be of the socketed variety.

In operation, the torque absorber is envisioned being used as follows. During the manufacture of the prosthesis, the socket 12 must be molded to a male mold of the amputee's stump. Accordingly, retainer 40 may be positioned a relatively small distance away from a male mold (not shown) so that the socket 12 may be molded thereabout (see particularly FIGS. 1, 4 and 5). Socket 12 encompasses the upper portion of elastomeric member 24 and also encompasses the entire exposed surface of retainer 40, in particular, the flanges 44 and 46. As previously noted, during the molding process of socket 12, flange 46 is tightened down against the upper end of elongated cylindrical member 26 so that the elastomeric member 24 serves to seal the area at the top of the bushing 32 and plastomeric sleeve 34. This sealing prevents inadvertent seepage of plastomeric material into that area, which could lock retainer 40 in a fixed relationship with hollow cylindrical member 22 and defeat the purpose of the torque absorber. Once the molding process is complete for socket 12' in the embodiment illustrated in FIG. 5, the set screw 64, which is of assistance to enable retainer 40 to be tightened, may be relieved. In the embodiment shown in FIG. 1 the flange 28 is accessible, hence a similar set screw is not necessary. It should now be apparent to those skilled in the art that socket 12 may rotate through the motion of retainer 40 which is lockingly associated with elongated cylindrical member 26 rotatably mounted in the hollow cylindrical member 22. The resiliency of elastomeric member 24 serves to return socket 12 to the neutral or center position once the prosthesis is lifted from the ground when used by an amputee.

Comparison between the embodiments depicted in FIGS. 4 and 6 is appropriate in that the torque absorber 12 is positioned at opposite ends of the above knee or upper pylon. The embodiment in FIG. 6 is preferred even though the mass of the torque absorber is located adjacent the knee rather than adjacent the socket. This embodiment may use a relatively light-weight plastic foam pylon 16' which is affixed to torque absorber 10 by, for example, an epoxy adhesive. The socket 12" which may be of glass fiber material is then formed about pylon 16' and torque absorber 10. The important feature seen in all the embodiments is the ability to mold the socket or socket extension over the elastomeric member 24 which is resiliently associated with prosthetic extremity by cylinder 22 while simultaneously bonding the same socket to retainer 40 which is rotatable in cylinder 22 and about the axis of the prosthetic extremity. The result provides for rotational movement of the socket relative the prosthetic foot with a simple resilient return arrangement.

Although this torque absorber has been shown in relation to a pylon or a knee joint, it is envisioned that the torque absorber may also be used in other positions in prostheses and should not be considered limited to the two applications nor to the particular embodiments described. Furthermore, it is to be understood that variations to the torque absorber are to be considered within the scope of this disclosure and are limited only by the following claims.

Embodiments of the invention in which an exclusive property or privilege is claimed are defined as follows:

1. A torque absorber for a prosthesis having a socket, the torque absorber comprising:

a first hollow cylindrical means for interconnection with the skeletal portion of the prosthesis;

second means rotatably mounted in said first hollow cylindrical means;

resilient means bondingly associated about said first hollow cylindrical means;

said second means and said resilient means bondingly moldable in said prosthesis socket so that said second means and said resilient means cooperate to allow limited rotation of said socket relative said first hollow cylindrical means.

2. The torque absorber of claim 1 further comprising plastomeric bearing means disposed between the first hollow cylindrical means and the second means.

3. The torque absorber as set forth in claim 2 wherein the hollow cylindrical means further comprises:

a first cylindrical portion adapted to receive the skeletal portion of the prosthesis; and a metallic gripping portion bondingly associated with the exterior of said first cylindrical portion.

4. The torque absorber as set forth in claim 3 wherein the first cylindrical portion of the hollow cylindrical means comprises clamping means distal of the first cylindrical portion for securely clamping the skeletal portion of a prosthesis.

5. The torque absorber of claim 4 wherein the second means comprises:

an elongated cylindrical member having a flanged head at one end, a cylindrical mid-portion, and a threaded end portion at the other opposite end, the threaded portion of lesser diameter than the cylindrical mid-portion; and axially bored retainer means threadably engageable on said threaded end so that with said second means disposed in said first hollow cylindrical means said axially bored retainer means may be disposed distal of the clamping means.

6. The torque absorber of claim 5 wherein the axially bored retainer means defines a pair of axially spaced apart flanges.

7. The torque absorber of claim 6 wherein the resilient means comprises an elastomeric cylindrical member having spaced apart first and second flanges, said first flange proximate the retainer means and defining a plurality of axial notches circumferentially oriented thereabout.

8. The torque absorber of claim 7 further comprising bushing means press-fitted interior of the first cylindrical portion, and wherein the plastomeric bearing means comprises a plastomeric sleeve disposed between said bushing means and the elongated cylindrical member and a pair of plastomeric washers.

9. The torque absorber of claim 8 wherein the first flange of the elastomeric cylindrical member extends above the bushing means a first distance, the cylindrical mid-portion with one of the plastomeric washers disposed between the flanged head and said bushing means extends a second distance above said bushing means relatively less than said first distance, and said other plastomeric washer disposed about cylindrical mid-portion proximate the threaded end and abutting said bushing means extends upwardly therefrom a third distance less than said second distance.

10. The torque absorber of claim 9 wherein the metallic gripping portion is comprised of a linked flexible member bonded circumferentially about the first cylindrical portion.

11. The torque absorber of claim 1 wherein the prosthesis includes a prosthetic knee joint, and further, wherein the hollow cylindrical means is bonded to said knee joint, the torque absorber further comprising lock means disposed in said knee joint and cooperating therewith for lockingly engaging the second means relative to said first hollow cylindrical means.

* * * * *